United States Patent [19]

Jones

[11] Patent Number: 5,064,370

[45] Date of Patent: Nov. 12, 1991

[54] MOLAR DISTALIZING APPLIANCE

[76] Inventor: Richard D. Jones, 1113 Taylor Ave., Godfrey, Ill. 62035

[21] Appl. No.: 685,526

[22] Filed: Apr. 15, 1991

[51] Int. Cl.$^5$ .............................................. A61C 3/00
[52] U.S. Cl. ........................................ 433/21; 433/18
[58] Field of Search ................... 433/5, 6, 17, 18, 19, 433/21, 23

[56] References Cited

U.S. PATENT DOCUMENTS

| | | | |
|---|---|---|---|
| 2,580,042 | 12/1951 | Paus | 433/21 |
| 4,017,973 | 4/1977 | Nelson | 433/18 |
| 4,255,139 | 3/1981 | Ladanyi | 433/21 |
| 4,424,031 | 1/1984 | Dahan | 433/18 |
| 4,525,143 | 6/1985 | Adams | 433/5 |
| 4,571,178 | 2/1986 | Rosenberg | 433/19 |
| 4,595,361 | 6/1986 | Blechman et al. | 433/18 |
| 4,975,052 | 12/1990 | Spencer et al. | 433/21 |

Primary Examiner—John J. Wilson
Attorney, Agent, or Firm—Lloyd L. Zickert

[57] ABSTRACT

A molar distalizing appliance for distalizing the first and/or second molars into a normal anterior/posterior relationship with the opposing teeth, which is cantileverly mounted from the first molar and includes a spring means activated by a connection to an anchoring tooth such as a first or second bicuspid or a deciduous molar as a tooth mesial to the molar. The distal end of the appliance is formed to mount in a stabilized position on the molar and to extend mesially along the mesially positioned teeth to a point that permits development of a light continuous force from the spring sufficient to bodily move the first and/or second molars distally from the bicuspid.

24 Claims, 2 Drawing Sheets

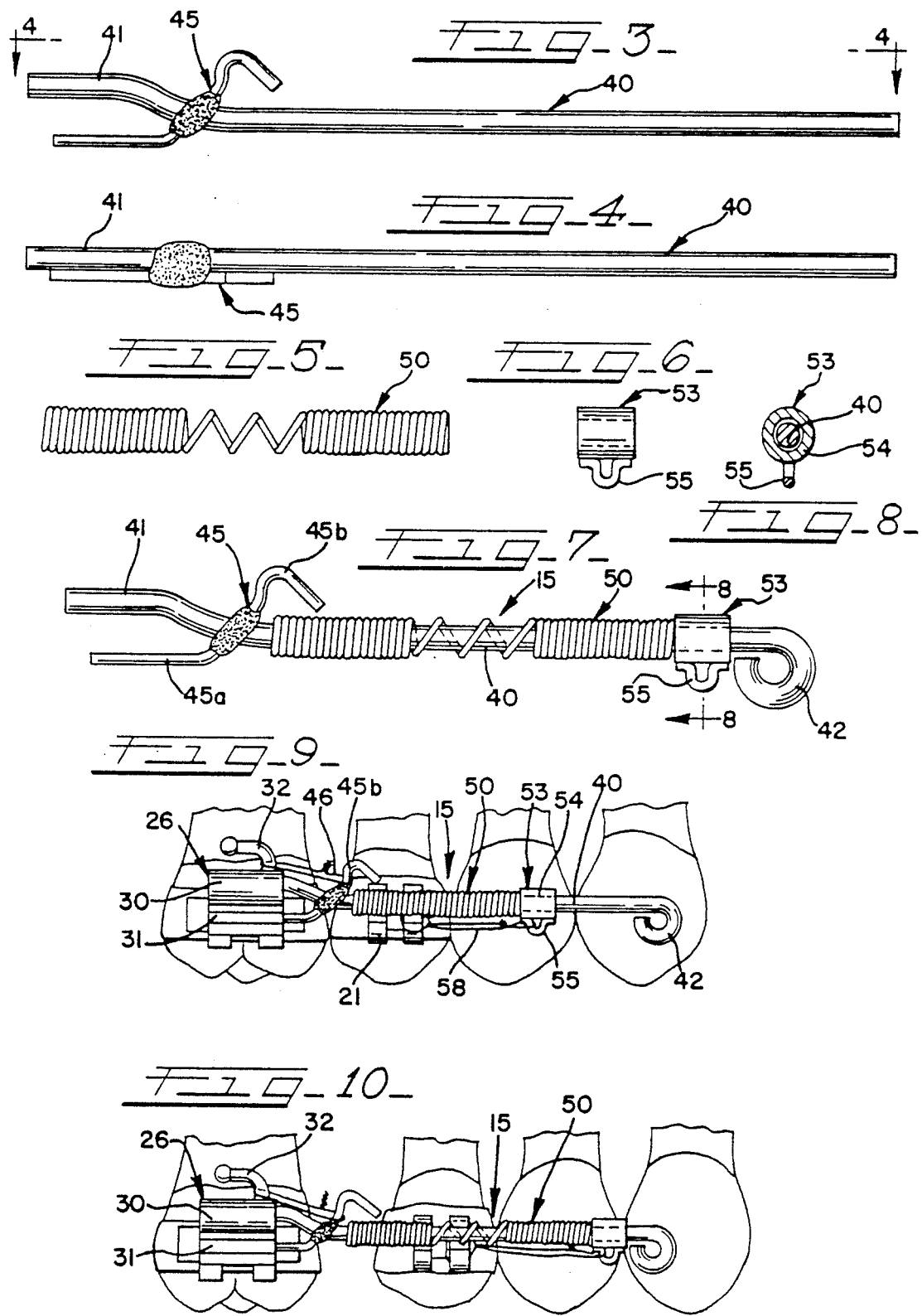

MOLAR DISTALIZING APPLIANCE

DESCRIPTION

This invention relates in general to an orthodontic appliance for distalizing molars, and more particularly to an appliance for effecting distalization of the molars without requiring any cooperation of the patient, and still more particularly to an appliance that is cantileverly mounted from the first molar and includes spring means activated by the connection to the mesial anchor tooth.

BACKGROUND OF THE INVENTION

Heretofore, distalizing molars has normally been accomplished with appliances that require good patient cooperation. For example, it has been well known to distalize molars through the use of headgear apparatus. Such headgear apparatuses include a face bow that is worn externally of the mouth and needs to be placed by the patient during times of wearing the appliance. It is also known that headgear appliances apply relatively heavy discomforting forces that sometimes inhibit the patient from wearing the headgear. Obviously, if the headgear appliance is not worn by the patient, it will not be effective in accomplishing the distalization of molars. It is also known that headgear apparatus can cause serious patient injuries due to face bow displacement.

Magnets have also been used to distalize molars, but use of such systems requires the use of bulky devices which are sometimes discomforting to wear and impair the facial profile. Moreover, the magnets produce substantially greater forces that can be uncomfortable.

SUMMARY OF THE INVENTION

The present invention achieves the desired distalization of molars without the necessity or dependence on patient cooperation, and also by the use of light forces. Further, the invention is much safer than headgear devices because it is worn entirely within the mouth. The molar distalizing appliance of the invention is mounted on an arch in activated condition to provide distalization of the molars without the need for adjustment or manipulation by the patient. The appliance is aesthetically acceptable because it is received entirely within the mouth and cannot be visually observed when the mouth is normally opened for talking as the appliance is positioned principally along the posterior teeth.

Further the appliance is compact in nature and would at the most minimally affect facial profile. The appliance of the invention utilizes a nickel titanium spring which produces continuous light forces that are generally comfortable to the patient.

The molar distalizing appliance of the invention includes a main wire or bar receivable at the distal end in a headgear tube mounted on a molar to be moved and having a stabilizing device at the distal end to stabilize the orientation of the appliance. A nickel titanium coil spring for providing a light continuous force is telescopically received on the main wire. The spring is bottomed at the distal end and a sliding collar is telescopically received on the main wire to bear against the mesial end of the spring. Activation of the spring is accomplished by ligating the sliding collar to an anchor tooth mesial to the molar such that the spring is under compression. The anchor tooth may be a bicuspid or a deciduous molar, and anchoring may be produced by use of a Nance appliance, a thermoformed retainer, or a modified Hawley retainer.

The distalizing appliance of the invention is normally used on the upper arch, but it could be used on the lower arch if desired. It is also normally used in pairs, that is, one on each side of the upper arch but may be used singly if desired.

It is therefore an object of the present invention to provide a new and improved molar distalizing appliance for distalizing molars which does not depend or rely on patient cooperation.

A further object of the present invention is in providing a molar distalizing appliance that is worn entirely within the mouth along the posterior teeth, thereby making the appliance more aesthetically pleasing than those distalizing appliances that require external devices.

A still further object of the present invention is in the molar distalizing appliance that is activated by the orthodontist during a patient visit and which is capable of producing a continuous light force that enhances patient comfort.

Another object of the invention is in the provision of a molar distalizing appliance that may be easily and quickly mounted in place and activated, thereby minimizing chair time.

Still another object of the invention is in the provision of a molar distalizing appliance for efficiently distalizing the first and/or second molars into a normal anterior/posterior relationship with the opposing teeth and which is activated by the orthodontist and requires no adjustment on the part of the patient when it is being worn.

Another object of the invention is to provide a distalizing appliance that is entirely safe to wear, thereby avoiding injuries to the patient.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 3 is an elevational view of the main wire or bar or appliance of the present invention with the stabilizing and tieback wire mounted on the distal end;

FIG. 4 is a top plan view of the main archwire of FIG. 3 and looking generally in the direction of the arrows 4—4;

FIG. 5 is an elevational view of the coil spring that is used on the main wire of the appliance;

FIG. 6 is a side elevational view of the sliding collar that is used on the main wire for activating the coil spring;

FIG. 7 is a side elevational view of the entire appliance where the wire and sliding collar are mounted in place and the mesial end of the main wire is bent to prevent the removal of the spring and sliding collar;

FIG. 8 is a vertical sectional view taken substantially along line 8—8 of FIG. 7;

FIG. 9 is a side elevational view of the distalizing appliance of the invention mounted in place on the first molar and illustrating the appliance in activated state where the sliding collar is tied back to an appliance on the bicuspid; and FIG. 10 is a successive view to FIG. 9 in that it shows the molar to have been moved distally of the bicuspid and that the spring is now in expanded and rest position.

DESCRIPTION OF THE INVENTION

Figure 1:
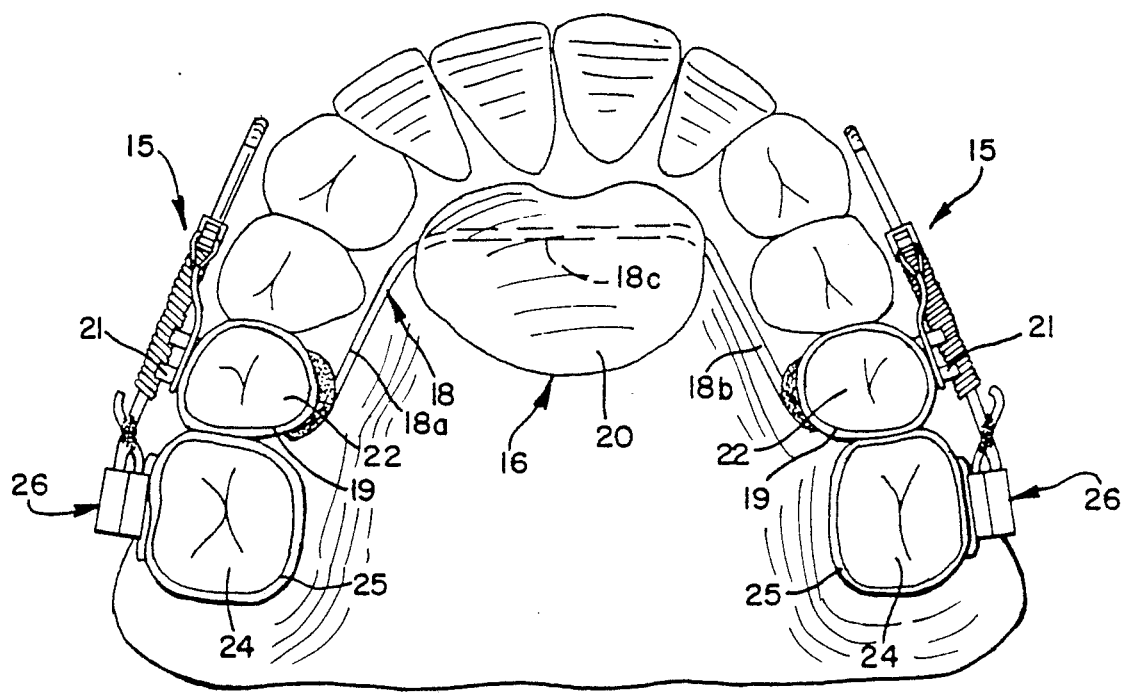
FIG. 1 is a bottom plan view of the upper arch illustrating the use of a Nance appliance for anchoring the bicuspids and the use of a pair of molar distalizing appliances according to the present invention in mounted relation on the upper arch.

The molar distalizing appliance of the present invention is used in conjunction with an appliance that anchors the second bicuspids or teeth mesial to the molars to be moved. They may be anchored with a Nance appliance, a modified Hawley retainer, a thermoformed retainer, or any suitable appliance. The appliance will be described and illustrated for use on the upper arch, although it will be appreciated it could be used on the lower arch if desired. The appliance may be used only on one side or simultaneously on both sides.

At a first visit with a patient, bands are chosen for fitting the upper first molars and upper second bicuspids or other anchor teeth mesial to the molars such as deciduous molars. An impression is taken of the upper arch, from which a model of the upper teeth can be made. Where a Nance appliance is used for anchoring the second bicuspids, it is made and fitted to the model of the upper arch. The Nance appliance includes a lingual wire of about 036 inch in size and formed between the bicuspid bands and soldered at the lingual surface of the bands. An acrylic button is formed in the palatal portion of the U-shaped lingual wire to bear against the tissues of the upper palate at the anterior of the arch. Preferably, the Nance button is formed to extend laterally to within three to five millimeters of the first bicuspids and upper canines. A suitable tieing device, such as a bracket, button, hook or the like, is secured to the buccal of the bicuspid bands.

Next, the appropriate molar distalizing appliance will be chosen for each side, and in the initial stage it will merely include the main archwire or bar with the stabilizing wire and tieback hook mounted on the buccal side. The main archwire and bar may then be formed to be as close to the canine as possible so that it will minimize irritation of the lips. Thus, it may be bent in a curve to generally match the buccal plane of the posterior teeth. The coil springs may then be mounted on the main archwire together with the sliding collars, after which the mesial ends of the main archwires can be bent into an eyelet or the like to act as a stop so that it will be stopped. Preferably, the mesial end of the main archwire will, after being stopped, be terminated at the canines, although it could terminate at another point depending on the length of the spring used. A molar tube appliance will be secured to the buccal of the molar bands.

When the patient comes in for the next visit, the bands will then be cemented to the anchor teeth such as the upper second bicuspids, and to the upper first molars. By cementing the bands to the upper second bicuspids, that will accomplish installation of the Nance appliance. A suitable bracket, button, eyelet, cleat, or the like for fastening one end of the activating ligatures will be mounted on the buccal of the second bicuspid bands for purposes of tying a ligature to activate the distalizing appliance. It should be appreciated the activating ligature could be connected to a tooth other than the second bicuspid. Suitable molar tube appliances will be on the buccal of the first molar bands when they are cemented into place. These molar tube appliances will include at least a headgear/bumper tube, a main archwire or auxiliary tube, and optionally a hook.

The distalizing appliances are then mounted in position by inserting the distal end of the main wire into the headgear tube and then the stabilizing wire into the main archwire or auxiliary tube. A ligature is tied between the hook on the main wire and the hook on the molar tube appliance in order to secure the appliance in place on the first molars. This prevents accidental displacement and possible ingestion of the appliance by the patient.

The appliance is then activated by tying a ligature between the sliding collar and the bracket or other device on the anchor tooth or second bicuspid band. The spring will be compressed as desired to apply a light force. Thereafter, the patient may return in four to five weeks for adjustment of the coil springs if they are open and particularly if no tip is noticed of either the bicuspids or molars. It is important to maintain the molar tieback so that the appliance is stabilized relative to the molar tube appliance.

Figure 2:
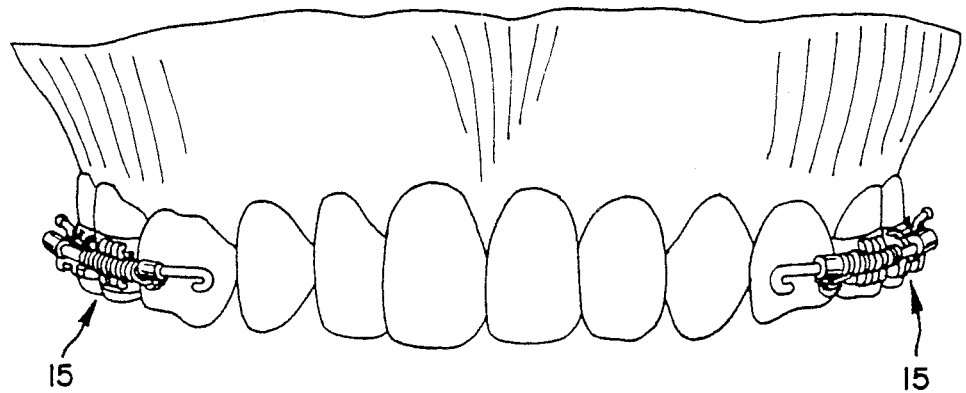
FIG. 2 is a front elevational view of the upper arch of FIG. 1.

Referring now to the drawings and particularly to FIGS. 1 and 2, the distalizing appliance or jig of the present invention is generally indicated by the numeral 15 and shown in mounted relation on the first molars of the upper arch in FIGS. 1 and 2 and activated by the second bicuspids. Also, a Nance appliance 16 is shown in FIG. 1 and used for the purpose of anchoring the second bicuspids, it being appreciated that other anchoring appliances may be used, such as a thermoformed retainer or a modified Hawley retainer. These various teeth-anchoring devices are well known in orthodontics and can be applied to any sets of opposing teeth wherever anchoring is desired. While the anchoring appliance shown and described is used to anchor second bicuspids, it should be appreciated it could be used to anchor first bicuspids or deciduous molars if desired. Further, while the appliance or jig of the invention is shown and described for distalizing upper or maxillary molars, it could be used for distalizing lower or mandibular molars also.

The Nance appliance 16 includes an inverted U-shaped wire 18 having arms 18a and 18b extending from a palatal portion 18c. The free ends of the arms are soldered to bicuspid bands 19. Preferably, the wire 18 will be 0.036 inch in diameter to provide the required strength and stiffness for a proper Nance appliance. A button 20 of suitable acrylic is carried on the palatal portion of the wire 18 and bears against the upper palate. A twin tie wing bracket 21 is mounted on the buccal side of the first bicuspid bands 19 and which will serve as an anchoring member for the activating ligature. It will be appreciated that other devices, such as a button, hook or the like, may be substituted for the bracket in order to provide a necessary device for tying the activating ligature. The second bicuspid bands 19 are suitably cemented to the second bicuspids 22.

Cemented to the first upper or maxillary molars 24 are molar bands 25, each of which has suitably mounted on the buccal side a suitable molar tube appliance 26. The molar tube appliance illustrated includes a headgear/bumper tube 30, hereafter referred to as a headgear tube, an main archwire tube or auxiliary tube 31, and a hook 32, as seen particularly in FIGS. 9 and 10. The hook 32 extends distally to facilitate the tying of a mesially extending ligature. As seen most clearly in FIGS. 9 and 10, the distalizing appliance of the invention is cantileverly mounted on the molar tube appliance 26 and extends mesially along the buccal surfaces of the second bicuspid, first bicuspid and canine teeth.

Referring most particularly to FIGS. 7 to 10, the molar distalizing appliance 15 of the invention includes a main wire or bar 40 having an offset portion 41 at the distal end and an eyelet 42 at the mesial end. The offset portion 41 is received in the headgear tube of the molar tube appliance and by being offset will only extend into the tube to the offset portion, as illustrated in FIGS. 9 and 10. Thus, the offset portion defines a stop. Further, the main body of the wire is then aligned with the teeth and away from the gingiva.

A stabilizing and tieback wire or hook 45 is soldered to the buccal side of the main wire 40 just mesial to the offset portion 41 such as to include a stabilizing wire 45a and a hook 45b. The stabilizing wire 45a generally parallels the offset portion 41 and is received within the main archwire tube or auxiliary tube 31 so as to function as a stabilizing member for the appliance and essentially prevent roll or rotation of the appliance relative to the molar tube appliance. Further, the stabilizing wire 45a is shorter than the offset portion 41 to facilitate placement of the appliance on the molar tube appliance. The tieback hook accordingly stabilizes the appliance or jig, preventing roll or rotation so that it can continue to provide a proper distalizing force. Preferably, as illustrated, the stabilizing wire 45a terminates short of the end of the offset portion 41 so that upon mounting of the distalizing appliance the offset portion is first inserted into the headgear tube and the appliance is oriented so that the stabilizing wire can then be inserted into the main archwire tube or auxiliary tube. The hook 45b enables a wire tieback ligature 46 to be tied between the molar tube appliance hook 32 and the distalizing appliance so that the distalizing appliance may be maintained in tightly seated position on the molar tube appliance when mounted in the mouth. Thus, the hook allows effective ligation of the jig or appliance to the buccal tube preventing dislodgment of the appliance.

Telescopically received on the main wire 40 is a coil spring 50 having a suitable number of coils and being of a suitable length so that it can be activated to produce a desired distalizing force. The distal end of the coil spring will bottom on the stabilizing and tieback wire 45.

A sliding collar 53 is telescopically received over the main wire 40 at the mesial end of the main wire and bottoms against the mesial end of the coil spring 50. The sliding collar includes a tubular body 54 that is sized for free sliding movement on the main wire and an eyelet 55 used for tying an activating ligature. A hook may be provided in place of the eyelet. As seen in FIG. 9 the steel activating ligature 58 is tied between the bracket 21 and the sliding collar by utilizing the eyelet 55. While the ligature is shown as being tied only to the mesial tie wing of the bracket 21, it should be appreciated that it could be tied to both tie wings if so desired. Also, it will be appreciated that the ligature 58 will be tied in such a manner as to compress the coil spring 50 a desired amount to produce the desired light force. As shown in FIG. 10, once the spring has done its work and the molar has been moved distally to define a space between the molar and the second bicuspid, the coil spring 50 will become inactive or passive.

While a hook 32 is illustrated on the molar tube appliance 26, it will be appreciated that the ligature 46 could be tied around the entire molar tube appliance if no hook was included.

All of the parts of the molar distalizing appliance 15 will be preferably made of stainless steel with the exception of the coil spring which will be made of nickel titanium and preferably continuous force nickel titanium. When the appliance is provided to the orthodontist, it will be in disassembled form, which will include the main wire 40 with the stabilizing and tieback wire 45 soldered in place, as seen in FIG. 3. After the main wire is fitted to the arch of the patient's model, the spring will be assembled on the main wire together with the sliding collar 55. Then, the eyelet 42, or appropriate shape to act as a stop so that the main wire is "stopped", can be formed at the mesial end to complete the assembly. The appliance is secured to the first molar by the tieback ligature wire 46, and then the activating ligature 58 is applied to suitably compress the spring.

Inasmuch as it is desired to have the stabilizing and tieback wire 45 mounted on the buccal side of the main wire, it will be appreciated that the appliance will be provided in two forms, one for the left side and one for the right side. It does not matter whether the headgear tube of the buccal tube appliance is mounted occlusally or gingivally as the appropriate appliance will be chosen in order to preferably place the stabilizing and tieback wire 45 on the buccal side when it is mounted in place.

The main wire is preferably 0.036 inch round stainless steel and about 35 millimeters in length. The stabilizing and tieback wire is preferably 0.016 or 0.020 inch round stainless steel and six to seven millimeters in length and soldered to the base wire 40. It is also preferably shorter by one to one-and-one-half millimeters of the distal end of the base wire 40. The spring 50 is preferably about 17 millimeters long and, as above mentioned, made of continuous force nickel titanium. The sliding collar 53 is made of stainless steel and preferably of 0.040 inch tube with approximately 0.035 inch eyelet. Thus, the sliding collar 50 may be stainless steel tubing about 3.2 millimeters in length with an approximately 0.035 inch loop soldered onto it to form the eyelet 55. The main wire is sized to be placed into a 0.045 inch headgear tube, while the 0.016 or 0.020 stabilizing and tieback wire is placed into the auxiliary tube or the main archwire tube. While the main wire is preferably round, it could be rectangular or polygonal if desired. Or, the distal end could be polygonal to fit in a polygonal tube and eliminate the need for the stabilizing wire.

Preferably, 0.011 or 0.012 inch stainless steel ligature wire is used to tie the appliance to the molar tube appliance, and preferably 0.009 or 0.010 inch stainless steel ligature wire is used to activate the coil spring by tying between the second bicuspid bracket 21 and the sliding collar 53. It will be appreciated that the coils of the coil spring will need to be compressed in order to apply a force to the first molar, but it is important that the coils not be overcompressed.

The nickel titanium spring 50 is highly resilient and will not take permanent deformation. Stainless steel springs can take a permanent set and further do not produce a uniform continuous force. Preferably, depending on its compression, it may provide forces up to about 90 grams. This is substantially less than headgear or magnets, the latter of which start at 250 grams.

The nickel titanium spring will produce through its deflective range of about 4 millimeters at least about 75 grams of force. Thus, a light continuous and uniform force is applied by the nickel titanium spring. Low or light forces substantially reduce tipping, root resorption, and periodontal ligament problems.

In view of the foregoing, it will be appreciated that the molar distalizing appliance of the invention, when mounted in place and activated, will not require adjustment by the patient during the time it is worn by the patient. Thus, patient cooperation is not needed to effectively use the appliance. While it is preferable that the appliance be used prior to the mounting of all of the brackets, it can be used at anytime during treatment. Often, it is desired to accomplish the distalizing of the molars at the beginning of treatment. Thus, the appliance of the invention will provide a more effective method of distalizing the molars in order to move the molars into the accepted Class I relationship with the lower molars. The appliance of the invention utilizes continuous light pressure to distalize the molars and wherein the light forces may be as low as 70 grams to open space for the developing or existing arch. Such low, gentle force is generally very comfortable to the patient. By providing effective molar distalization, treatment time can be minimized as well as the need for extractions. In addition to eliminating the necessity of patient cooperation, the appliance of the invention is essentially invisible. It also does not affect appreciably the facio-drape of the cheek muscles and is hygienic. Finally, by being fixed and not removable, it is entirely safe to the patient.

It will be understood that modifications and variations may be effected without departing from the scope of the novel concepts of the present invention, but it is understood that this application is to be limited only by the scope of the appended claims.

The invention is hereby claimed as follows:

1. A molar distalizing appliance for moving a molar distally, wherein the appliance is to be cantileverly mounted from the molar and extend along the buccal side of the teeth mesial to the molar, said appliance including a main wire for mounting at its distal end to the molar, stabilizing means on the main wire to be connected to the molar for stabilizing the appliance on the molar, spring means on the main wire stopped at the distal end at the molar, means for activating the spring means, and means for tieing the activating means to an anchor tooth mesial to the molar thereby applying a distalizing force to said molar.

2. The appliance of claim 1, wherein means is provided to anchor the distalizing appliance to the molar tube appliance.

3. The appliance of claim 1, wherein the spring means includes a coil spring telescopically received on the main wire.

4. The appliance of claim 3, wherein the activating means includes a sliding collar bearing against the mesial end of the coil spring.

5. The appliance of claim 4, wherein the collar is tied to the anchor tooth with a ligature.

6. A molar distalizing appliance for distalizing the first and/or second molars into a normal anterior/posterior relationship with opposing teeth, wherein means is provided to anchor opposing teeth mesial to the molars, and a molar tube appliance for mounting on one of the molars and includes at least a headgear tube and an auxiliary wire tube, said distalizing appliance comprising a main wire having an offset portion at the distal end received in the headgear tube, a stabilizing wire secured to the main wire and received in the main archwire tube or auxiliary tube of the molar tube appliance, a hook means on the main wire for coacting with the molar tube appliance to receive a ligature for ligating the distalizing appliance to the molar tube appliance, a coil spring telescopically received on the main wire and stopped at the distal end on the stabilizing wire, sliding means on the main wire engaging the mesial end of the spring, a ligature for ligating the sliding means to an anchor tooth such as to activate the spring and apply a distalizing force to the first and/or second molars.

7. The distalizing appliance of claim 6, wherein the mesial end of the main wire is stopped to prevent the sliding means from being displaced from the mesial end of the main wire.

8. A molar distalizing appliance for distalizing the first and/or second molars into a normal anterior/posterior relationship with opposing teeth, wherein means is provided to anchor teeth mesial to the molars, and a molar tube appliance for mounting on one of the first molars and includes at least a headgear tube and a main archwire tube or auxiliary tube, said distalizing appliance comprising a main wire having an offset portion at the distal end received in the headgear tube, means at the distal end of the main wire for stabilizing the main wire against rotation relative to the headgear tube, means on the main wire coacting with ligature means to ligate the distalizing appliance to the molar tube appliance, a coil spring telescopically received on the main wire and stopped at the distal end on the main wire, sliding means on the main wire engaging the mesial end of the spring, a ligature for ligating the sliding means to the anchor tooth such as to activate the spring and apply a distalizing force to the first molar.

9. The distalizing appliance of claim 8, wherein the stabilizing means includes a stabilizing wire received in the main archwire tube or auxiliary tube of the molar tube appliance, and the means on the main wire for ligating the distalizing appliance to the molar tube appliance includes a hook extending from the stabilizing wire.

10. The distalizing appliance of claim 8, wherein the sliding means includes a collar on the main wire having an eyelet or hook for receiving a ligature.

11. The distalizing appliance of claim 10, wherein the main wire, stabilizing wire and hook, and the collar with the eyelet are of stainless steel, and the spring is of nickel titanium.

12. The distalizing appliance of claim 10, wherein the spring is of a material capable of producing a light continuous force.

13. The distalizing appliance of claim 12, wherein the spring is of nickel titanium.

14. A molar distalizing appliance for distalizing the first and/or second molars into a normal anterior/posterior relationship with opposing teeth, wherein means is provided to anchor teeth mesial to the molars, and a molar tube appliance for mounting on one of the molars and includes at least a headgear tube and a main archwire tube or auxiliary tube, said distalizing appliance comprising a main wire received in the headgear tube and said main wire having means for preventing distal movement through the headgear tube, means at the distal end of the main wire for stabilizing the main wire against rotation relative to the headgear tube, means on the main wire coacting with ligature means to ligate the distalizing appliance to the molar tube appliance, a coil spring telescopically received on the main wire and stopped at the distal end on the main wire, sliding means on the main wire engaging the mesial end of the spring, a ligature for ligating the sliding means to the anchor tooth such as to activate the spring and apply a distalizing force to the first molar.

15. The distalizing appliance of claim 14, wherein the tooth anchoring means includes a Nance appliance.

16. The distalizing appliance of claim 14, wherein the tooth anchoring means includes a thermoformed retainer.

17. The distalizing appliance of claim 14, wherein the tooth anchoring means includes a modified Hawley appliance.

18. The distalizing appliance of claim 14, wherein the distalizing appliance main wire is formed to lie along the teeth mesial to the molar and to extend approximately to the canine.

19. The distalizing appliance of claim 14, wherein the distalizing appliance is for mounting on the upper arch.

20. The distalizing appliance of claim 14, wherein the distalizing appliance is for mounting on the lower arch.

21. The distalizing appliance of claim 19, wherein a distalizing appliance is for mounting on each side of the upper arch.

22. The distalizing appliance of claim 20, wherein a distalizing appliance is for mounting on each side of the lower arch.

23. The distalizing appliance of claim 14, wherein the coil spring is of a material capable of producing a light continuous force.

24. The distalizing appliance of claim 23, wherein the coil spring is nickel titanium.

* * * * *